United States Patent [19]

Davidson et al.

[11] Patent Number: 5,573,401

[45] Date of Patent: Nov. 12, 1996

[54] BIOCOMPATIBLE, LOW MODULUS DENTAL DEVICES

[75] Inventors: James A. Davidson, Germantown; Ajit K. Mishra, Memphis, both of Tenn.; Kenneth P. Daigle, Olive Branch, Miss.; Paul Kovacs, Memphis, Tenn.

[73] Assignee: Smith & Nephew Richards, Inc., Memphis, Tenn.

[21] Appl. No.: 260,707

[22] Filed: Jun. 16, 1994

Related U.S. Application Data

[63] Continuation-in-part of Ser. No. 36,414, Mar. 23, 1993, Pat. No. 5,509,933, which is a continuation-in-part of Ser. No. 986,280, Dec. 7, 1992, abandoned, which is a continuation-in-part of Ser. No. 647,453, Jan. 28, 1991, Pat. No. 5,169,597, which is a continuation of Ser. No. 454,181, Dec. 21, 1989, abandoned.

[51] Int. Cl.$^6$ ..................................................... A61C 8/00
[52] U.S. Cl. ..................... 433/201.1; 433/8; 433/18; 433/23; 433/173
[58] Field of Search ......................... 433/1–23, 173, 433/174, 176, 201.1, 202.1, 228.1

[56] References Cited

U.S. PATENT DOCUMENTS

| | | | |
|---|---|---|---|
| 2,892,706 | 6/1959 | Jaffe et al. | 420/418 |
| 2,987,352 | 6/1961 | Watson | 384/297 |
| 3,370,946 | 2/1968 | Bertea et al. | 420/418 |
| 3,408,604 | 10/1968 | Doi et al. | 335/216 |
| 3,643,658 | 2/1972 | Steinemann | 606/76 |
| 3,677,795 | 7/1972 | Bokros et al. | 427/2.24 |
| 3,752,664 | 8/1973 | Steinemann | 420/417 |
| 3,777,346 | 12/1973 | Steinemann | 73/866.1 |
| 3,849,124 | 11/1974 | Villani | 420/417 |
| 3,906,550 | 9/1975 | Rostoker et al. | 3/1.912 |
| 3,911,783 | 10/1975 | Gapp et al. | 420/417 |
| 4,040,129 | 8/1977 | Steinemann et al. | 433/173 |
| 4,145,764 | 3/1979 | Suzuki et al. | 623/16 |
| 4,170,990 | 10/1979 | Baumgart et al. | 606/78 |
| 4,197,643 | 4/1980 | Burstone et al. | 433/20 |
| 4,511,411 | 4/1985 | Brunner et al. | 148/237 |
| 4,857,269 | 8/1989 | Wang et al. | 420/417 |
| 4,902,359 | 2/1990 | Takeuchi et al. | 148/133 |
| 4,983,184 | 1/1991 | Steinemann | 623/66 |
| 5,169,597 | 12/1992 | Davidson et al. | 428/613 |
| 5,232,361 | 8/1993 | Sachdeva et al. | 433/8 |
| 5,252,066 | 10/1993 | Fairhurst | 433/8 |
| 5,429,501 | 7/1995 | Farzin-Nia et al. | 433/21 |

FOREIGN PATENT DOCUMENTS

| | | |
|---|---|---|
| 0437079A1 | 12/1990 | European Pat. Off. . |
| 2703529 | 8/1978 | Germany . |

OTHER PUBLICATIONS

Zwicker, et al., Z. Metallkunde, 61 (1970) pp. 836–847.
Collings, E. W., "The Physical Metallurgy of Titanium Alloys," *American Society for Metals*, pp. 40–41, 66–69, 72–73, 120–121, 190–191, 194–195, 214–215, 218–219, 226–227 (no date).
Collings, E. W., "The Physical Metallurgy of Titanium Alloys," *American Society for Metals*, pp. 68–70 (no date).
Albert, et al., Z. Metallunde, 62 (1972) 126.

(List continued on next page.)

*Primary Examiner*—Christopher A. Bennett
*Attorney, Agent, or Firm*—Pravel, Hewitt, Kimball & Krieger

[57] ABSTRACT

The invention provides dental devices (including implants, abutments, bridges, screws, and orthodontic appliances) that are fabricated from low modulus, biocompatible, non-toxic Ti-Nb-Zr alloys. The dental implants provide a biomaterial-to-bone interface that results in significant attachment between implant and bone. The implants may be supplied with a porous coating or macro-texture to further promote bone attachment and stabilization of the implant in the jaw bone. Other orthodontic appliances such as brackets and wires have improved elastic toughness and corrosion resistance so that they provide superior performance and corrosion characteristics.

40 Claims, 4 Drawing Sheets

OTHER PUBLICATIONS

Brown & Merritt, "Evaluation of Corrosion Resistance of Biology," Case Western Reserve University, 13 Feb. 1986 (1:8).

Mears, "Electron–Probe Microanalysis of Tissue and Cells from Implant Areas," *JNL of Bone and Joint Surgery*, vol. 48B, No. 3, pp. 576–576 (Aug. 1966).

Ferguson, Laing, and Hodge, "The Ionization of Metal Implants in Living Tissues," *JNL of Bone and Joint Surgery*, vol. 42A, No. 1, pp. 77–90 (Jan. 1960).

Hoar and Mears, "Corrosion–Resistant Alloys in Chloride Solutions: Materials for Surgical Implants," pp. 506–507.

Kirk–Othmer Encyclopedia of Chemical Technology, vol. 23, pp. 98–113.

Jepson, et al., The Science & Tech., Titanium Ed. Jaffee, et al., Pergamon, N.Y., 1968, p. 677.

Heller, et al., Jour. Less Common Metals, 24 (1971) 265.

Van Noort, R., Jour. Mat. Sci., 22 (1987) 3801.

The Japan Medical Review, vol. 12, (undated) unnumbered page, pp. 12, 23.

Author Unknown, "Titanium–Niobium Base Quaternary Alloys," (date unknown), pp. 405–419.

BIOCOMPATIBLE, LOW MODULUS DENTAL DEVICES

RELATED APPLICATIONS

This application is a continuation-in-part of U.S. Ser. No. 08/036,414, filed Mar. 23, 1993, now Pat. No. 5,509,933, which is in turn a continuation-in-part of U.S. Ser. No. 07/986,280, filed Dec. 7, 1992, now abandoned, which is in turn a continuation-in-part of U.S. Ser. No. 07/647,453, filed Jan. 28, 1991, issued as U.S. Pat. No. 5,169,597 on Dec. 8, 1992, which is in turn a continuation of U.S. Ser. No. 07/454,181, filed Dec. 21, 1989, now abandoned.

BACKGROUND OF THE INVENTION

1. Field of the Invention

The invention provides dental devices, including orthodontic devices, associated restorative components and implants, of enhanced biocompatibility, corrosion resistance, and low modulus. More specifically, the invention provides dental devices, of all kinds, fabricated from a biocompatible, low modulus alloy containing predominantly titanium, niobium, and zirconium in specified amounts.

2. Description of the Related Art

Intraoral conditions provide a challenging environment for dental implants and other orthodontic and restorative devices, both from a chemical-biochemical and a mechanical-biochemical viewpoint. Nevertheless, standard dental implants and restorations are expected to last for the long term (greater than 10 years) in spite of severe conditions that include exposure to temperature ranges from about 5 to about 55° C.; pH ranges from acid to base (3–10); multi-directional high forces (as high as about 2–24 N); stresses as high as 30,000 psi (207 MN/m$^2$); and an average chewing cycle rate of about 80 per minute (i.e., in excess of about 10$^5$ per year).

Most early dental restorations, predating 1950, failed clinically within a few years because of clinical, technical, or material-based conditions. The introduction of relatively inert cast cobalt alloys (Co-Cr-Mo), wrought titanium, titanium alloy (Ti-6Al-4V), aluminum oxide ceramic, carbon, and some polymers (primarily polymethyl methacrylate (PMMA)) increased longevity to an extent that they are now judged acceptable by clinical standards. Some of these devices have remained functional for decades.

It has been found that one-stage devices, those functionally loaded within 1–3 weeks after permanent placement into bone, demonstrate fibrous tissue growth adjacent to most biomaterial interfaces. These fibrous tissue zones are apparently caused by premature mechanical load-induced interfacial motion during bone healing. In contrast, under passive or non-functionally loaded conditions, most biomaterials demonstrate direct bone interfaces. When these devices are subsequently loaded for function, after a 3–6 month period of passive healing, interfaces evolve to remain as remodeled bone (osteointegration takes place) or subsequently change to soft tissues, depending upon the implant design, biomaterial, and host characteristics. Interface alteration from one tissue type to another (i.e., from bone to fibrous tissue), is dependent on both loading type (compression, tension, or shear) and magnitude.

Some investigators propose that fibrous tissue zones along dental implant biomaterial interfaces provide an important and favorable role related to force transfer. Therefore, fibrous tissue zones adjacent to dental implants have been called "pseudo periodontal ligaments."

Biomaterial-to-tissue interface conditions and attachment can be grouped as follows: (i) interfaces that demonstrate no attachment between biomaterial and bone, such as iron and cobalt alloys, polycrystalline aluminum and zirconium oxides, carbon and carbon silicon, and polymers; (ii) slightly attached interfaces, such as titanium and its alloys, alumina, and the like; and (iii) significantly attached interfaces, such as calcium-phosphate ceramics, bioglass, and glass-ceramics. It is suggested that interfacial attachment and stability are not solely dependent on the material surface but also require optimum implant design, materials, and clinical treatment.

There remains a significant need for new biomaterials to improve dental implants and devices and to provide for certain conditions that cannot be readily and effectively treated over the long term with available systems. Desirably, the biomaterials should have properties more similar to bone, be non-toxic and biocompatible, and implants of the biomaterials should have surfaces that allow development of a strong and stable bond to bone and soft tissues. Additionally, the materials should have excellent corrosion resistance coupled with high strength and toughness to withstand the rigors to which dental devices such as implants, abutments, attachment screws, orthodontic fixtures, wires, braces, bridges and the like, are subject in vivo. Many of these devices are subject to wide pH variations in the oral cavity and it is further desirable that they should be resistant to corrosion to avoid ion release into the body and also avoid producing a "metallic taste" in the mouth.

SUMMARY OF THE INVENTION

The invention provides dental devices including dental implants, restorative devices, orthodontic appliances, and dental tools. The devices of the invention are fabricated from low modulus biocompatible metal alloys that have moduli of elasticity closer to that of bone, and significantly less than that of commonly used steel, cobalt and Ti-6Al-4V alloys. More specifically, the devices of the invention are fabricated from Ti-Nb-Zr alloys that are highly biocompatible, due to the absence of alloying components that are known or suspected of having low biocompatibility or even toxicity. Preferably, these Ti-Nb-Zr alloys are cold worked to improve strength and hardness while maintaining low modulus and high corrosion resistance.

Aside from the low modulus, biocompatible, and non-toxic nature of the devices of the invention, the surfaces of dental implants according to the invention are preferably textured to provide for bone attachment so that they may be more readily stabilized in the oral cavity. Thus, the surfaces may be coated with beads, wire mesh, and the like to encourage bone ingrowth.

The preferred Ti-Nb-Zr alloys used to fabricate devices of the invention are disclosed in U.S. Pat. No. 5,169,957, commonly owned, which is hereby fully incorporated by reference. The alloys include the component metals titanium, niobium and optionally zirconium. Consequently, it is preferred that the alloys contain an amount of zirconium, in excess of levels normally found as an impurity in titanium or niobium. Niobium is an important component since its addition to the alloy, in specified amounts, produces a low modulus. Tantalum may be substituted for the niobium, but niobium is preferred. Thus, for a low modulus, the alloys desirably contain from about 10 to about 20 wt. % as the sum of niobium and tantalum (i.e. the tantalum proportion could be zero so that only niobium is present). In an alternative range, the sum of niobium and tantalum is from about 35 to about 50 wt. %. Among the preferred of these alloys useful in the invention dental devices are those titanium alloys that conform to the following composition: Titanium, from about 10 to about 20 wt. % niobium, and less than about 20 wt. % zirconium, although higher amounts of zirconium are useful. Thus, alloys may contain up to about 45 wt. % zirconium or more.

More preferably, these alloys contain from about 2 to about 20 wt. % zirconium, most preferably about 8 to about 18 wt. % zirconium. Further, although the useful alloys are referred to as "Ti-Nb-Zr" alloys, it must be understood that this designation encompasses the substitution of all or part of the Nb with Ta.

The titanium alloys containing a higher range of niobium content, i.e. from about 35 to about 50 wt. %, also provide low modulus and are useful in the dental devices of the invention. Again, at least a portion of the niobium may be replaced by tantalum, but niobium is preferred.

The low modulus, biocompatible alloys may be worked by metal-working processes to enhance their properties. For example, U.S. Ser. No. 08/036,414 filed Mar. 24, 1993, commonly assigned, and hereby fully incorporated by reference, teaches how to improve the strength of the Ti-Nb-Zr alloys by hot working.

Contrary to expectation, cold-working of the Ti-Nb-Zr alloys useful in the invention reduces stiffness (modulus) significantly and increases strength while maintaining biocompatible and corrosion resistant characteristics. Thus, the hexagonal close packed alloy can be cold worked up to about 90%, but cold working to between 30 and 60% is preferred to reduce the stiffness (modulus) and improve the strength of the alloy while retaining good ductility and corrosion resistance.

Diffusion hardening techniques harden the surfaces of dental devices of the invention for resistance to abrasives typically found in dentrifices. Methods of diffusion hardening are discussed in U.S. Pat. No. 5,372,660, filed Aug. 26, 1993, and issued Dec. 13, 1994, hereby fully incorporated by reference. Other surface hardening techniques may also be utilized.

Due to their enhanced biocompatibility, low modulus, and non-toxicity, the implants of the invention, depending upon their design, permit ready bone attachment and reduce the tendency to form fibrous tissue adjacent to the implant surfaces to any significant extent. As a result, the implants fall within the "significantly attached" category that includes other highly biocompatible materials (such as calcium-phosphate ceramics, bioglass, and glass-ceramics) in that the implant-tissue interface demonstrates significant attachment. However, since implants of the invention are of metal alloy, the implants are significantly stronger, tougher, and more resistant to masticating conditions, to which dental implants are routinely subject, than implants of these other highly biocompatible materials. Further, it is expected that the implants of the invention will be long-lived and that they may not require replacement during the lifespan of the recipient. Thus, sequential surgical procedures to replace and repair dental implants may be minimized when implants according to the invention are used.

The invention also provides other dental devices made of the Ti-Nb-Zr alloy. These include dental wires for orthodontic applications, braces, bridges, abutments, attachment screws, and the like. These devices are biocompatible, corrosion resistant, low modulus, high strength and abrasion resistant. As indicated, tantalum can be used as a partial or complete substitute for the niobium content of the alloy, but niobium is preferred over tantalum. Thus, the alloy contains no elements that are toxic or suspected of being toxic, and has improved corrosion resistance as compared to pure titanium, Ti-6Al-4V, Ti-Mo alloys, and Ti-Ni alloys. Because of the high corrosion resistance, dental devices of the invention have less metal taste caused by metal ion release due to corrosion.

Furthermore, dental wires of the invention alloy are readily weldable to orthodontic brackets. Alloys such as Ti-Mo have inferior weldability due to segregation of the alloying elements and softening (less strength) in the weld compared to the invention Ti-Nb-Zr alloy. A major drawback of Ti-Ni alloy wires is that they are essentially non-weldable.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENTS

Figure 1:
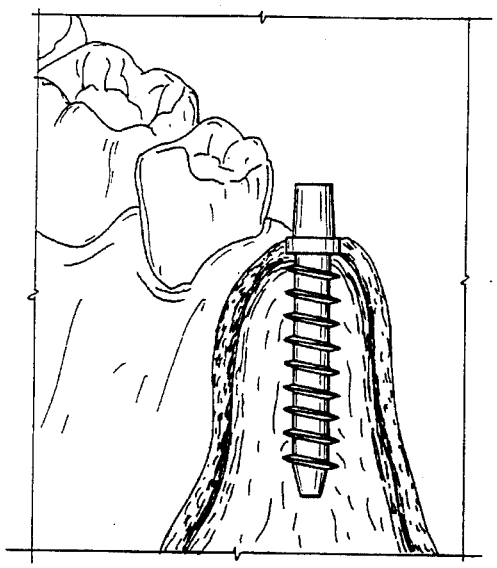
FIG. 1 shows a partial cross section of a gum with a dental implant fabricated from Ti-Nb-Zr alloy according to the invention, wherein the root of the implant is implanted into the jaw bone and an abutment projects above the gum line for receiving a crown.

The invention provides low modulus, biocompatible, non-toxic dental devices such as implants and other restorative and orthodontic appliances fabricated from specific Ti-Nb-Zr alloys and methods for using these dental devices.

The invention is equally applicable to a wide variety of dental implant designs, including, for example, the neckless blade implants shown in U.S. Pat. No. 5,165,892; the mandibular osteoimplants shown in U.S. Pat. No. 5,194,000;

and the like. Thus, implants according to the invention, may be made of any design, as long as they are fabricated from a low modulus, biocompatible, Ti-Nb-Zr alloy of the specified composition with a predominantly hexagonal close packed crystal structure. Preferably, these alloys conform to the following composition: Titanium, from about 10 to about 20 wt. % niobium, and up to about 20 wt. % zirconium. While the niobium content of the allow is critical for providing low modulus, the zirconium content is not. Zirconium is added to strengthen the alloy and may be present in any amount sufficient to produce the required strengthening effect, this amount may range from close to zero up to about 50 wt. %, but is preferably restricted to the range of about 2 to about 20 wt. %. More than about 20 wt. % zirconium does not significantly affect strength properties and produces an alloy of substantially equivalent properties.

More preferably, therefore, the alloys contain from about 2 to about 20 wt. % zirconium, most preferably about 8 to about 18 wt. % zirconium, to act as a strengthener. As explained in U.S. Pat. No. 5,169,597, incorporated by reference, a proportion of the niobium may be replaced with tantalum, without deleterious effect on implant properties, in particular the low modulus, but niobium is preferred. Thus, when tantalum is added, then the sum of tantalum and niobium is at least about 10 wt.% and at most about 20 wt. %. The most preferred alloys are in the range Ti-11Nb-11Zr to Ti-15Nb-15Zr, especially Ti-13Nb-13Zr.

U.S. Pat. No. 5,169,597 contains a description of the low modulus Ti-Nb-Zr alloys useful in the present invention. It should be noted that tantalum may be substituted for some or all the niobium in the useful alloys but that niobium is preferred. The term "low modulus" refers to a modulus of less than about 90 GPa, preferably less than about 85 GPa.

Dental devices according to the invention are preferably fabricated from cold worked titanium-niobium-zirconium alloy. The cold working process increases the ratio of strength to modulus to greater than about 2.0. By comparison, this ratio known as the flexibility (spring-back ratio) of the metal, is 0.87 for Ti-6Al-4V and about 1.8 for room temperature Beta Ti-Mo alloys. In particular, the flexibility of Ti-13Nb-13Zr is about 2.25, after the alloy has been cold worked for about 50–90%. The % cold work is defined as $(\Delta A/A_o) \times 100$, where $\Delta A$ is the change in cross-sectional area and $A_o$ is the initial cross-sectional area. Cold working may be carried out by processes such as drawing, forging, stamping, rolling, extruding, rotary swaging and the like to achieve a high degree of elastic toughness. It is preferred that the Ti-Nb-Zr alloys useful in the present invention be cold worked above about 30%, most preferably above about 40%.

The cold working process is preferably performed at ambient temperature, but may also be performed at temperatures up to about 300° C.

The cold worked Ti-Nb-Zr alloys useful in the invention may optionally be subjected to an aging heat treatment to increase their strength while maintaining a relatively low modulus. This aging treatment is more useful if the amount of engineering strain produced by the cold working process is less than about 50%. The cold worked (or cold worked and aged) titanium alloys useful in the invention preferably have a low elastic modulus (about 30 to about 90 GPa) and have tensile strengths exceeding about 700 MPa, preferably exceeding about 800 MPa.

The cold working operation may be applied either during production of the mill-product (e.g. bar, plate, strip, sheet etc.) and the dental devices machined from this mill-product, or it can also be applied during the fabrication of the device using a net-shape or near-net-shape forging process.

Further, the cold worked titanium alloy implants may be surface hardened as described in U.S. Pat. No. 5,372,660, incorporated by reference as if fully set forth. This may most preferably be performed during the aging heat treatment of the cold worked devices or implants. However, certain surface hardening treatments such as nitrogen ion implantation, and oxygen ion implantation and ceramic coatings such as titanium nitride, titanium carbide, zirconium dioxide, diamond-like carbon and the like may also be performed at or near ambient temperature after the aging heat treatment.

In the most preferred embodiments of the invention, cold working is performed in the Ti-Nb-Zr alloy which is in the water quenched condition, i.e. it has been rapidly cooled in water from above about 500° C. after either heat treatment or hot working at that temperature, as described in our copending related application U.S. Ser. No. 08/036,414, hereby fully incorporated by reference, filed on Mar. 24, 1993.

In a particularly preferred aging process, the Ti-Nb-Zr alloy is prepared by gradually heating the cold worked alloy from ambient temperature to about 200–550° C., followed by isothermal aging at that temperature for a time sufficient to develop the required strength and hardness while preserving the low modulus.

Certain of the surface hardening processes, such as diffusion hardening, may require heating that may increase the modulus and decrease the strength of a cold worked Ti-Nb-Zr alloy (especially if the % cold work is relatively high) by a phenomenon called overaging. This may be acceptable if wear resistance is an important requirement for the particular application and the design of the device is such that it has adequate strength despite the strength reduction caused by overaging. If this reduction in strength is not acceptable, techniques other than those that entail heating the alloy to any significant extent should be used to produce surface hardness. These techniques include providing titanium nitride coatings, ion implantation, and the like.

The desirability of using the Ti-Nb-Zr alloy according to the invention for the implant portion of an artificial tooth includes its improved corrosion resistance, biocompatibility, low modulus, and high strength compared to currently used Ti and Ti-6Al-4V alloys. Further, the alloy has demonstrated improved bone apposition qualities in animal studies over pure titanium, and thus improved stability of the dental implant in the jaw bone is expected. Restorative abutments are attached to the implant portion of the overall tooth replacement. The abutment is attached using an abutment screw, and a porcelain veneer is cemented or otherwise attached to the abutment to form the artificial tooth portion of the implant.

There are additional factors which render the invention unique and desirable over the use of current Ti and Ti-6Al-4V metals and gold alloys for dental implant, abutment, screws, and bridges. The invention devices can be surface hardened (as described herein) to further improve corrosion resistance (about ten times better than for Ti-6Al-4V), and reduce fretting wear from micromotion between mating components. Fretting wear can lead to premature loosening and even fracture of the implant components. Surface hardening is desirable for the abutment component of the tooth replacement to improve abrasion resistance to cleansers and cleaning instruments, as well as providing improved bonding to the porcelain or ceramic veneers which form the crown.

One of the unique features of the invention Ti-Nb-Zr dental devices is the combination of improved corrosion resistance (over a wider pH range, and crevice conditions), low-modulus and high-strength properties.

When an abutment screw is used to attach the crown (with abutment) to the implant, or the bridge to the implant, the ability of the system to remain tight is extremely critical to the success of the implant or restoration system. Poor tightening characteristics can lead to loosening and failure of the tooth implant system. In conventional screw design, the predominant factor governing structural integrity is material strength. That is, a screw can be tightened to about 50–75 percent of its ultimate tensile strength. The Ti-Nb-Zr alloys used in the invention devices, with their high tensile strength (above 910 MPa) can provide screw tightenability and integrity, similar or superior than that for Ti-6Al-4V. Lower strength Ti and gold alloys have lower tensile strength and are less suitable under these screw tightenability or integrity performance criteria.

There are also other factors associated with the screw and the clamped components (i.e., abutment or bridge and the implant) which contribute to the overall integrity. One factor is the ratio of the yield strength to the tensile strength. If, for example, the yield strength is less than about 75 percent of the ultimate strength, then creep (plastic deformation) and stress relaxation can occur, leading to subsequent loosening. Although Ti and gold alloys provide good screw tightening pressure, they tend to exhibit this limitation. In contrast, the invention devices, because they are made of the Ti-Nb-Zr alloy, particularly in the cold-worked condition, can exhibit a ratio of yield to tensile well above 75 percent depending on cold-work level and can reach 90–95 percent. Additionally, the Ti-Nb-Zr alloys used in the invention possesses excellent ultimate strength, typically above about 1025MPa and with a reduced elastic modulus (between about 45 GPa and 90 GPa). This modulus is substantially lower than that of Ti (about 105 GPa) Ti-6Al-4V (about 115 GPa), and gold alloy (about 99 GPa). Thus, the Ti-Nb-Zr alloy has a preferred yield:tensile ratio, high strength for improved screw integrity, and its exceptionally low elastic modulus reduces the tension exerted by the screw to produce excellent clamping pressure between the abutment screw, implant and abutment. The load carrying capability of a screw (or bolt) is not related to the same factors as those that describe the ability to simply tighten the screw or bolt to high levels without breaking it. The material properties of the material being tightened (i.e., abutment and implant) also affect the integrity and separation resistance of the tooth (or other structure) assembly. This is described below.

When bolt material "B" is used to make a screw or bolt and to apply a tightening load to a clamped material "C" (i.e., abutment to the implant), there are two forces that result under service (chewing) conditions. The first is the internal force from the tightened screw ($F_i$) and the other is the external force ($F_t$) resulting from service loads. The total force ($F_t$) is related to $F_i$ and $F_e$, and also to the elastic properties of the screw ($K_B$) and the material being tightened ($K_c$):

$$F_T = F_i + F_e/(1+K_c/K_B) \qquad (1)$$

The values of $K_B$ and $K_A$ relate to the elasticity of the engaged materials and their dimensions, where:

$$K_{B,C} = (\text{Area})(E_{C,B})/(\text{Length}) \qquad (2)$$

When tightening a screw or bolt, the tightening torque should be such that the internal load is greater than the external counter load to avoid separation (loosening). If these forces are equal, then we can calculate the stress within the bolt ($\tau\sigma$) that occurs when the surfaces are not separated, but just ready to do so, where:

$$\tau\sigma = F[1.35 + 1/(1+K_C/K_B)](1/\text{Area}) \qquad (3)$$

By using a limit of 50 percent of the limiting material tensile strength (the lower strength material) as the allowable screw stress level, the various forces (F) at just reaching separation of the components can be calculated, and are summarized in Table 1 for the case of 0.5 inch diameter (arbitrary) screw with 13 threads per inch. In Table 1, the values for $D_c/K_B$ are based on a given (arbitrary) screw geometry but with the elastic moduli of the various metals as indicated. Abbreviations include:

$E_B$=Bolt (or screw) modulus $E_C$=Modulus of the clamped material

SS=3 16 S. Steel

AU=Gold alloy

CPT=Pure Ti

T64=Ti-6Al-4V alloy

13/13=Ti-13Nb-13Zr (alloy used in certain embodiments of the invention) Note that the unique elastic and strength properties of the Ti-Nb-Zr alloy dramatically improve this separation force.

TABLE 1

Comparison load carrying capability (F) of various screw and assembly materials.

| BLT/MATL | $E_B$ | $E_C$ | $K_C/K_B$ | STRESS | AREA | F(Fe = Fi) |
|---|---|---|---|---|---|---|
| 13/13 | 6.5 | 6.5 | 3.47 | 70000 | 0.1257 | 5590.52 |
| 13/13* | 6.5 | 11.5 | 6.13 | 70000 | 0.1257 | 5904.54 |
| 13/T64 | 6.5 | 16.5 | 8.80 | 70000 | 0.1257 | 6059.67 |
| CPT/T64 | 15.0 | 16.5 | 3.81 | 47000 | 0.1257 | 3792.49 |
| CPT/CPT | 15.0 | 15.0 | 3.47 | 47000 | 0.1257 | 3753.64 |
| T64/CPT | 16.5 | 15.0 | 3.15 | 4700 | 0.1257 | 3713.53 |
| AU/CPT | 14.3 | 15.0 | 3.64 | 47000 | 0.1257 | 3773.28 |
| 13/CPT | 6.5 | 15.0 | 8.00 | 47000 | 0.1257 | 4043.38 |

Table 1 shows that the load carrying capability of Ti-Nb-Zr alloy abutment screw is superior to that for CPT, Ti-6Al-4V, and gold alloy screws when securing a Ti or Ti-6Al-4V implant. Additionally, the invention alloy screw shows improved load carrying capability when securing the other Ti-Nb-Zr implants and abutments. Although load carrying capability is slightly better when the invention screw material is securing a Ti-6Al-4V implant (as would be the case for a stainless steel or Co alloy implant), the use of these alloys for the implant component of the tooth system is less desirable than the invention alloy due to elastic modulus, bone attachment, and corrosion differences as discussed earlier.

For the case of orthodontic wire and brace devices, a combination of high strength and low modulus is desirable to more effectively control relocation and positioning of the teeth. A lower elastic modulus reduces pressure against the tooth over a wider range of tooth displacement, and reduces movement pain. Stainless steel wires have been gradually replaced by lower modulus titanium and titanium alloy wire. Ti-Ni alloy wires have been widely utilized for these applications, but contain Ni, an undesirable alloying constituent required to provide a memory to this alloy. Many patients have a sensitivity to nickel. Nickel also interferes with the natural passivation process of the titanium, and thus reduces the ability of this alloy to form an optimum passive surface oxide which is corrosion resistant in a wide range of acid and base (pH) conditions, including crevice conditions commonly present in dental devices (e.g., wire in contact with a bracket, or a bridge screwed to an abutment, etc.). Burstone (U.S. Pat. No. 4,197,643) describes a beta titanium alloy with a combination of high strength and low modulus (well below $20 \times 10^6$ psi) to improve elastic displacement compared to 316 stainless steel wire. Although Burstone claims a modulus between $8-16 \times 10^6$ psi, and that the beta alloy should be stabilized with stabilizing amounts of metal selected from the group Mo, Nb, Ta and V, the preferred beta alloy compositions are given as Ti-11.5Mo-6Zr-4.5Sn, Ti-13V-11Cr-3Al, and Ti-8Mo-8V-2Fe-3Al. As for the case of Ti-Ni alloy, the presence of the Mo, V, Cr and Fe can reduce the corrosion resistance of the titanium alloy over the wide pH conditions and crevice conditions associated with these devices. Additionally, beta titanium alloys are difficult to machine due to their work hardening tendencies, which hinders the manufacturability.

The Ti-Nb-Zr alloy described for use in the present invention contains Nb to improve corrosion resistance, strengthen the alloy, and minimize the modulus, particularly in the cold worked condition. Zr is added to strengthen the alloy, slow the transformation process during cooling to produce alpha martensite (vs. beta as in beta alloys described by Burstone), improve corrosion resistance, and increase the pH range over which the alloy will possess improved corrosion resistance. Importantly, the addition of Nb and Zr produces a titanium alloy which possess a homogenous structure of alpha prime martensite (hexagonal close packed) upon rapid cooling from above the beta transus temperature (about 735° C.). This is in contrast to "beta Ti alloys" described by Burstone, in which the microstructure which forms at room temperature is the beta phase (body centered cubic). According to Burstone, it is desirable to produce the beta structure due to its well-known workability. However, this structure readily strain hardens which makes machining of these type beta alloys relatively difficult. In contrast, the hexagonal close-packed crystal structure of the alloys used in the invention possess fewer slip systems resulting in less strain hardening and improved machinability. Such a crystal structure would not be expected to readily accommodate moderate-to-heavy mechanical workings (i.e., cold-working) due to their limited slip systems compared to "beta Ti" alloys. For example, Ti-6Al-4V alloy is an "alpha plus beta" alloy with both phases present, including a hexagonal close packed alpha phase. Consequently, it is very difficult to mechanically work this alloy. However, the alloys with alpha prime martensite that are used in the invention's dental devices can readily be cold worked greater than 85 percent. Thus, the alloys useful in the invention provide improved corrosion resistance and workability, as well as an improved combination of strength and modulus over prior art Ti alloys.

Finally, the elements Nb and Zr (and some tantalum is acceptable) are more uniformly mixed and distributed within the titanium base composition in the useful hexagonal close packed Ti-Nb-Zr alloys, in contrast to the strong tendency for "beta" titanium alloys that exhibit segregation (poorer mixing, less uniformity) due to the presence of strong beta stabilizers such as Cr, Fe, Mo and V. Such segregation can lead to variable and occasionally unpredictable properties of these "beta" Ti alloys.

For orthodontic brackets, used to secure orthodontic wire, it is important that corrective orthodontic wires move easily (low friction) relative to brackets to maintain force as the teeth gradually reposition themselves. Stainless steel and even Ti-Mo, Ti-Ni, Ti-6Al-4V, pure Ti, and other titanium alloys used for brackets tend to seize and gall, producing high friction and restrictive motion of the wire. Pure ceramic brackets have been proposed to overcome these problems. However, these are quite brittle relative to ductile metals and may break and become inoperative.

The invention dental devices of Ti-Nb-Zr alloy, in addition to improved corrosion resistance over a wider pH range, can be surface hardened as described above. The hard, ceramic surface reduces friction, while the bracket maintains a high level of ductility and fracture resistance due to the metal Ti-Nb-Zr substrate beneath the hard, low-friction surface. Thus, it is possible, depending on specific needs, to use the Ti-Nb-Zr alloy for orthodontic brackets, with or without surface hardening. The invention Ti-Nb-Zr alloy brackets and wires may also be further coated with a lubricous coating of silver, boron or boric acid to reduce friction.

Figure 1A:
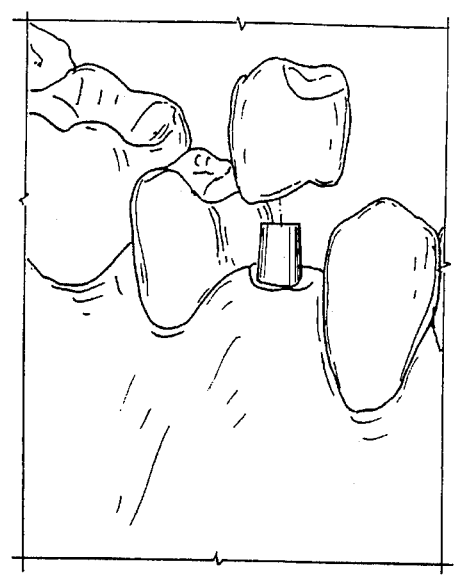
FIG. 1A shows a crown being positioned on an abutment that projects above the gum line.

Certain aspects of the invention may be more readily understood with reference to the accompanying-Figures, all of which are not to scale but for illustrative purposes only. FIG. 1 shows a fixture 10 implanted into a jawbone. The fixture 10 is capped with an abutment 12 for receiving a crown 14, as shown in FIG. 1A. In a typical implantation procedure, assuming that the original tooth has been removed, an incision is made into the gum above the implant site. The site is prepared by peeling back gum tissue and drilling into the jaw bone. A fixture is then screwed or pressed into place in the jaw bone and the site is covered for about 3 to about 6 months to allow bone to grow around the implant and stabilize it in the jaw bone. After this period, the top of the fixture 10 is exposed and an abutment 12 is attached to the fixture. A crown 14, having a socket corresponding to the abutment, is then anchored to the abutment to complete the method of implantation, as shown in FIG. 1A.

Figure 1B:
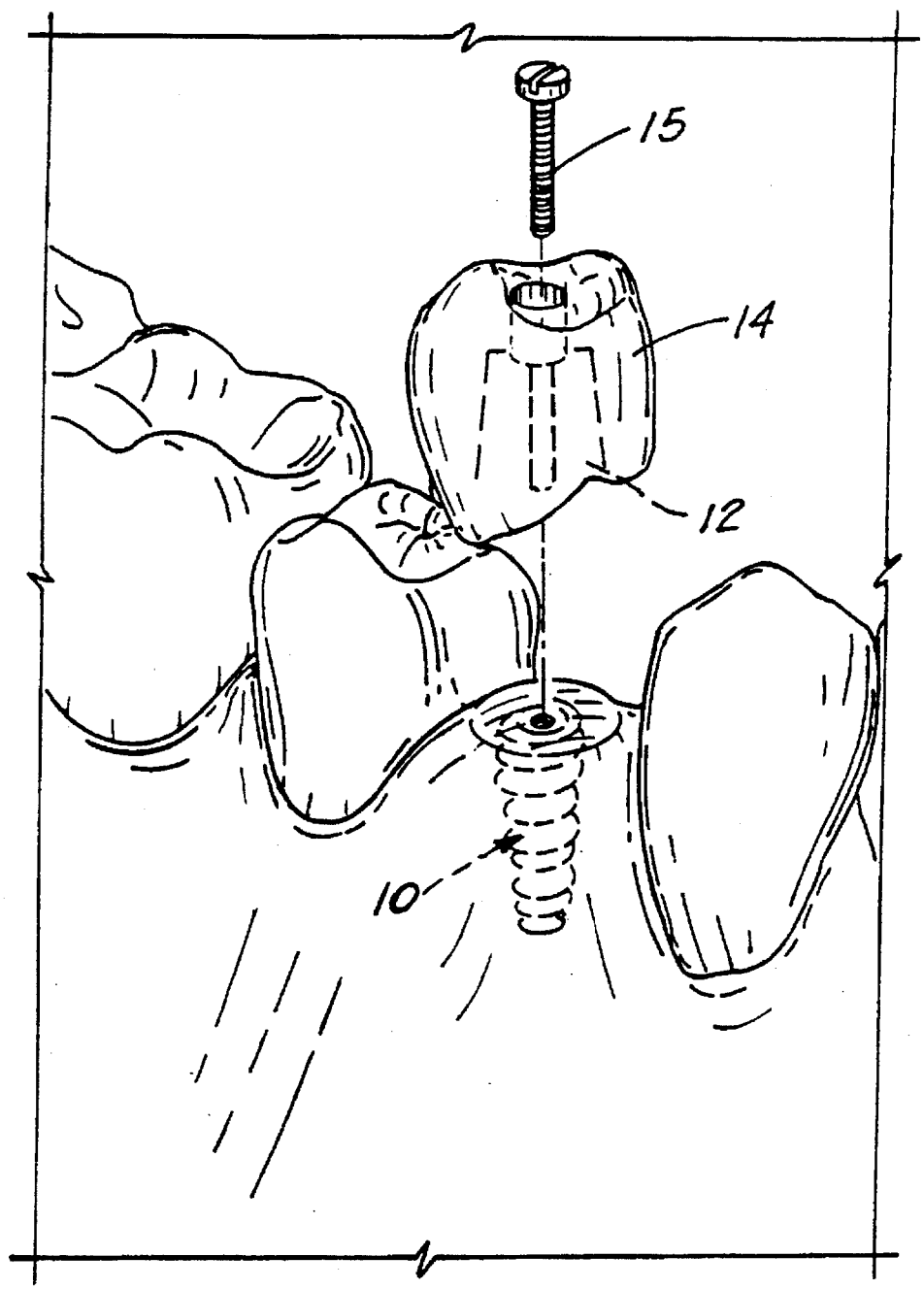
FIG. 1B shows a crown with an abutment and porcelain veneer in tooth-shape for attaching to an implant with an abutment screw, according to the invention fabricated from Ti-Nb-Zr alloy.

According to the invention, the fixture is prepared from a Ti-Nb-Zr alloy. Further, the fixture may be provided with a porous metal or macro-textured surface coating to promote bone attachment and anchoring of the fixture in place. The abutment 12 and any screws 15 are also fabricated from Ti-Nb-Zr alloys, as shown in FIG. 1B. The crown 14, in FIG. 1B, is fabricated to include an abutment made from Ti-Nb-Zr alloy, that is suitably coated to provide the appearance of a natural tooth. The alloys useful in the invention have been shown to have improved attachment to porcelain veneers compared to currently used gold-alloy substrates. For gold alloy crowns, the alloys have also shown the ability to effectively bond to gold alloy. This coating may be carried out by any conventional dental restorative techniques, coating with a ceramic or porcelain pigment, gold alloy, and polymeric bonding material, and the like. Wear-resistant coatings are disclosed in U.S. Pat. 5,169,597.

The low modulus and high strength of the Ti-Nb-Zr alloy enhances the attachment and clamping pressure of the abutment screw to the abutment and reduces the possibility of loosening.

The invention also provides dental bridges that may require more than one fixture and abutment. In this circumstance, bridge is prepared that includes all the teeth that must be replaced.

Figure 2:
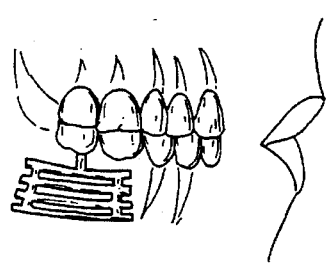
FIG. 2 shows a blade or plate (placed in bone), and fabricated from a Ti-Nb-Zr alloy, according to the invention.

As shown in FIG. 2, blades or plates 20 may be placed in bone. These blades or plates 20 are also fabricated from Ti-Nb-Zr alloys.

Figure 3:
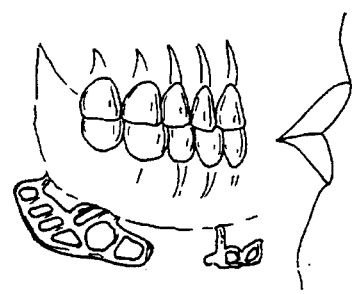
FIG. 3 is a subperiosteal implant according to the invention fabricated from a Ti-Nb-Zr alloy.
Figure 4:
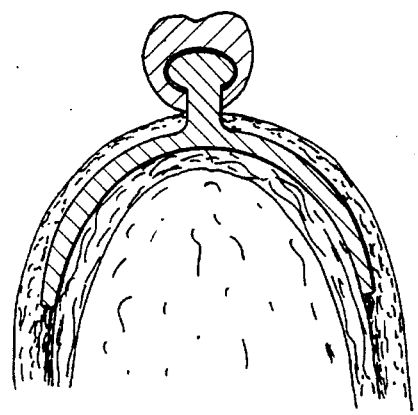
FIG. 4 shows a saddle-shaped implant body with projecting neck and abutment for receiving a crown according to the invention fabricated from Ti-Nb-Zr alloy.

FIG. 3 shows a subperiosteal implant 30, placed over the jaw bone, that is fabricated from Ti-Nb-Zr alloys according to the invention. The placement of a subperiosteal implant can be more easily seen from FIG. 4, which shows a saddle-shaped implant body 40 straddling the cortical bone 42 and covered by gingival tissue 44. The saddle-like implant body 40 has a neck 45 terminating in an abutment connector 46. A crown 48 is placed over the abutment connector to complete the dental implant. According to the invention, the implant body 40, neck 45, abutment connector 46, and crown 48 may all be beneficially fabricated from Ti-Nb-Zr alloys. The body 40 may be coated with a porous coating or use a macrosurface texture to promote bone attachment to stabilize the implant in place.

Figure 5:
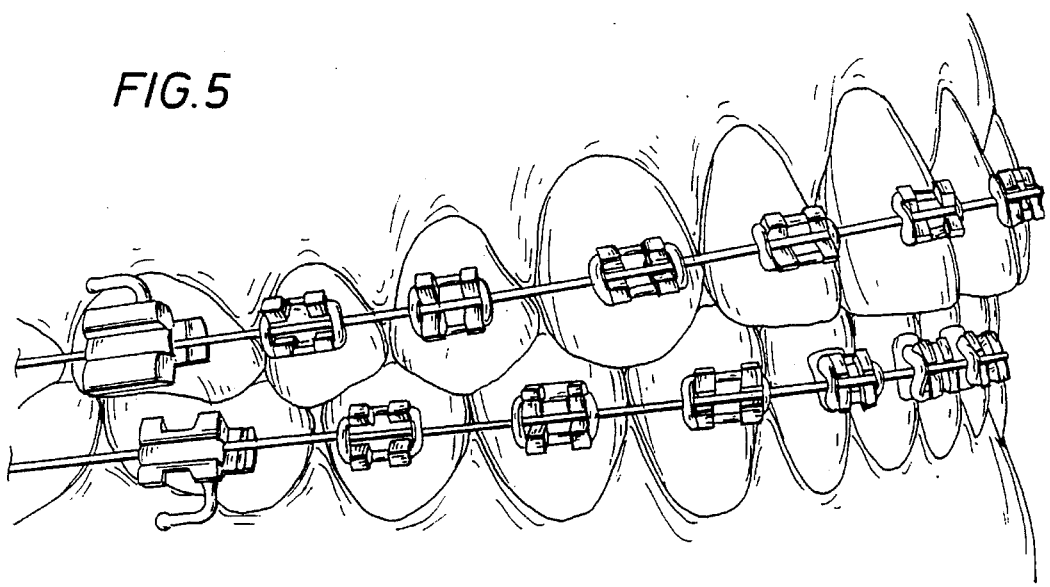
FIG. 5 is an illustration of brackets according to the invention fabricated from Ti-Nb-Zr, and orthodontic arch wires engaging the brackets, are also fabricated from Ti-Nb-Zr, according to the invention.

FIG. 5 shows an orthodontic assembly including arch wires 51 engaged with various orthodontic brackets 50 and buccal tubes 52. The arch wires, orthodontic brackets and buccal tubes according to the invention are fabricated from Ti-Nb-Zr alloys. These orthodontic appliances may also be coated with silver, boron, or boric acid or other biocompatible surface lubricant to reduce friction between the arch wire, orthodontic brackets and buccal tubes.

Figure 6A:
FIGS. 6A–6C show a variety of contoured molar bands fabricated from Ti-Nb-Zr according to the invention.
Figure 6B:
Figure 6C:
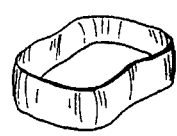

FIGS. 6A, 6B and 6C show a variety of contoured molar bands which, according to the invention, are fabricated from Ti-Nb-Zr alloys to improve ease of attachment, in that they are more readily inserted around crowns in preparation than are Ti, gold alloy, or Ti-6Al-4V bands and have higher spring-back to assure proper attachment.

Figure 7:
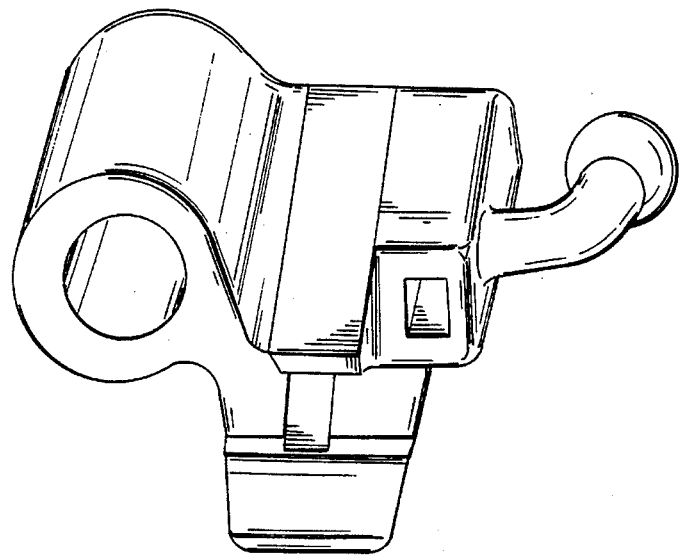
FIG. 7 is an example of a mini-buccal tube according to the invention fabricated from Ti-Nb-Zr alloy.

FIG. 7 is an enlarged view of a typical mini-buccal tube fabricated from Ti-Nb-Zr alloy, according to the invention.

Figure 8A:
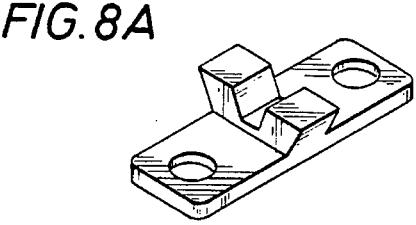
FIGS. 8A–8C are several examples of dental brackets according to the invention fabricated from Ti-Nb-Zr.
Figure 8B:
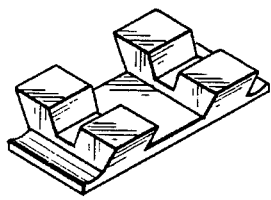
Figure 8C:
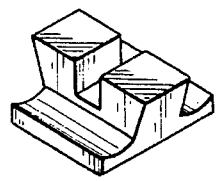

FIGS. 8A–C show specific embodiments of orthodontic brackets. Orthodontic brackets, according to the invention, are fabricated from Ti-Nb-Zr alloys.

Figure 9A:
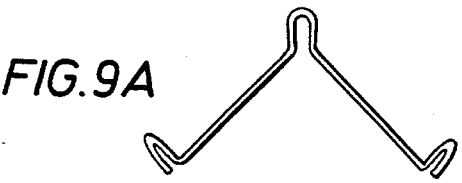
FIGS. 9A–9C are examples of orthodontic wires according to the invention fabricated of Ti-Nb-Zr alloy.
Figure 9C:
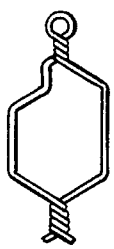
Figure 9B:
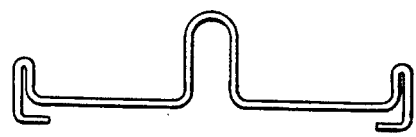

FIGS. 9A–C show embodiments of orthodontic wires. According to the invention, orthodontic wires are fabricated from Ti-Nb-Zr alloys for improved positioning of the teeth. The orthodontic wires provide improved deflection (or "flexibility") as compared with Ti-6Al-4V (2.25 versus 0.87) and also with respect to Beta titanium alloys (2.25 Versus 1.8). Thus, the wires are able to provide constant tension over a wider range of deflection while reducing the level of pain to which the patient is subject when the wires are in use. Additionally, these wires, as indicated above, may be coated with silver, boron, boric acid, or other biocompatible lubricant, or subjected to nitrogen ion implantation, or coated by chemical or physical vapor deposition of hard surface layers to reduce friction. Typical wires according to the invention range in thickness from about 0.005 to about 0.05 inches in diameter.

Although the invention has been described with reference to its preferred embodiments, those of ordinary skill in the art may, upon reading this disclosure, appreciate changes and modifications which may be made and which do not depart from the scope and spirit of the invention as described above and claimed below.

The following examples are intended to illustrate the invention above and claimed below and are not intended to limit the scope of the invention in any way.

EXAMPLE 1

Several 1" thick round cornered square bars of Ti-13Nb-13Zr, were solution treated at 800° C. and water quenched, to produce a soft and more workable material, and were cold rolled to 0 9", 0.08" and 0 6" thicknesses which resulted in engineering strains of approximately 10%, 20% and 40% respectively. The reduction per pass in this case was 0.00625". Some of these bars were also subjected to a subsequent aging heat treatment at temperatures ranging from 300° C. to 500° C. Their properties after cold working, both with and without subsequent aging, are given in Table 1:

TABLE 1

|  | 1 | 2 | 3 | 4 | 5 | 6 |
| --- | --- | --- | --- | --- | --- | --- |
| Bar Thickness (in.) | 0.9 | 0.8 | 0.6 | 0.9 | 0.8 | 0.6 |
| e (%) | 10 | 20 | 40 | 10 | 20 | 40 |
| Aging Time (h) | 0 | 0 | 0 | 6 | 6 | 6 |
| Aging Temp. (°C.) | — | — | — | 500 | 500 | 500 |
| UTS (MPa) | 848 | 919 | 952 | 889 | 886 | 890 |
| YS (MPa) | 709 | 799 | 807 | 807 | 807 | 839 |
| Δl (%) | 18 | 16 | 15 | 17 | 19 | 17 |
| RA (%) | 68 | 67 | 61 | 60 | 66 | 61 |
| E (GPa) | 52.2 | 55.2 | 50.7 | 67.3 | 76.3 | 74.6 |
| Rc | 21 | 20 | 20 |  |  |  |
|  | 7 | 8 | 9 | 10 | 11 | 12 |
| Bar Thickness (in.) | 0.9 | 0.8 | 0.6 | 0.9 | 0.8 | 0.6 |
| e (%) | 10 | 20 | 40 | 10 | 20 | 40 |
| Aging Time (h) | 1 | 1 | 1 | 6 | 6 | 6 |
| Aging Temp. (°C.) | 500 | 500 | 500 | 400 | 400 | 400 |
| UTS (MPa) | 921 | 921 | 938 | 935 | 956 | 1001 |
| YS (MPa) | 832 | 841 | 878 | 830 | 852 | 915 |
| Δl (%) | 16 | 17 | 14 | 17 | 14 | 15 |
| RA (%) | 60 | 60 | 50 | 50 | 48 | 51 |
| E (GPa) | 68.3 | 66.9 | 66.1 | 64.9 | 61.0 | 59.7 |
| Rc | 30 | 30 | 32 |  |  |  |
|  | 13 | 14 | 15 | 16 | 17 | 18 |
| Bar Thickness (in.) | 0.9 | 0.8 | 0.6 | 0.9 | 0.8 | 0.6 |
| e (%) | 10 | 20 | 40 | 10 | 20 | 40 |
| Aging Time (h) | 1 | 1 | 1 | 1 | 1 | 1 |
| Aging Temp (°C.) | 400 | 400 | 400 | 300 | 300 | 300 |
| UTS (MPa) | 921 | 953 | 1026 | 865 | 911 | 951 |
| YS (MPa) | 816 | 856 | 939 | 722 | 793 | 790 |
| Δl (%) | 15 | 15 | 10 | 18 | 17 | 15 |
| RA (%) | 58 | 56 | 32 | 64 | 68 | 65 |
| E (GPa) | 63.6 | 59.1 | 60.5 | 54.8 | 55.1 | 52.0 |
| Rc | 33 | 33 | 34 |  |  |  | e = Engineering Strain (% Cold work)
UTS = Ultimate Tensile Strength
YS = Yield Strength
Δl = Elongation
RA = Reduction in area
E = Elastic Modulus
Rc = Rockwell C hardness As seen from the results given above, an ultimate tensile strength of 1026 MPa with a very low modulus of 60.5 GPa was produced on aging a 40% cold worked material for one hour at 400° C. Thus when Ti-13Nb-13Zr is solution treated above its beta transus temperature and water quenched, it can achieve a high strength, very low modulus condition on subsequent working and aging.

EXAMPLE 2

A 1.25" diameter Ti-13Nb-13Zr bar was solution treated at 800° C. and water quenched. The hardness after water quenching was Rc 15–17. The bar was centerless ground to 1.21" diameter to remove surface oxides and subjected to a series of cold working steps, as described below.

The bar was cold rolled 41% to a round cornered square. The round cornered square was cleaned, solution treated, and water quenched, surface ground and cleaned again, and then swaged to 0.585" diameter. The swaged bar was hot straightened, solution heated, water quenched, and centerless ground to 0.44" diameter. The bar was then swaged to 0.25" in diameter which represented 68% cold reduction. Some of this bar was also subjected to a subsequent aging heat treatment at temperatures ranging from 300° C. to 500° C.

A hot worked, water quenched 1" diameter bar was cold drawn to 0.70" diameter, resulting in an engineering strain of 51%.

The tensile properties of both bars, both with and without subsequent aging, are given in Table 2:

TABLE 2

|  | 1 | 2 | 3 | 4 |
|---|---|---|---|---|
| Bar diameter (in.) | 0.25 | 0.25 | 0.25 | 0.70 |
| e (%) | 68 | 68 | 68 | 51 |
| Aging Time | 0 | 6 h | 20–75 min | 0 |
| Aging Temp. (°C.) | — | 500 | 300–400 | — |
| UTS (MPa) | 1003 ± 3 | 934 ± 3 |  | 1051 ± 3 |
| YS (MPa) | 924 ± 21 | 862 ± 0 |  | 989 ± 10 |
| Δl (%) | 15 ± 0 | 10 ± 5 |  | 11 ± 1 |
| RA (%) | 59 ± 2 | 36 ± 24 |  | 46 ± 3 |
| E (GPa) | 46.9 ± 1.1 | 66.5 ± 2.3 |  | 44.4 ± 0.3 |
| Rc |  | 30 | 25.1–27.5 |  | e = Engineering Strain (% Cold Work)
UTS = Ultimate Tensile Strength
YS = Yield Strength
Δl = Elongation
RA = Reduction in Area
E = Elastic modulus
Rc = Rockwell C hardness As shown in Table 2, 68% cold worked Ti-13—13 has outstanding properties, good strength and ductility with a very low modulus of 46.9 GPa. This is about 40% of the modulus of Ti-6Al-4V (115 GPa) and lower than that of even Al alloys (70 GPa). However, aging for six hours at 500° C. did not increase the strength any further, in fact it caused a decrease in strength and an increase in modulus.

The 51% cold drawn material had even more impressive properties, with an UTS of 1051 MPA and a modulus of 44.4 GPa.

EXAMPLE 3

Some 0.75" diameter bars which had been hot rolled and water quenched were cold swaged to 0.375" and 0.25" diameter, which corresponds to engineering strains of 75% and 89% respectively. Some of these specimens were subjected to various aging cycles. The tensile properties of these bars, both with and without subsequent aging, are given in Table 3:

TABLE 3

|  | 1 | 2 | 3 | 4 | 5 |
|---|---|---|---|---|---|
| Bar Diameter (in.) | 0.375 | 0.375 | 0.375 | 0.375 | 0.375 |
| e (%) | 75 | 75 | 75 | 75 | 75 |
| Aging Time (h) | 0 | 1 | 1 | 1 | 1 |
| Aging Temp. (°C.) | — | 350 | 400 | 450 | 500 |
| UTS (MPa) | 1038 ± 10 | 1031 | 1021 | 994 | 953 |
| YS (MPa) | 989 ± 3 | 1004 | 998 | 941 | 916 |
| Δl (%) | 12 ± 2 | 12 | 14 | 16 | 18 |
| RA (%) | 44 ± 6 |  |  |  |  |
| E (GPa) | 48.4 ± 2.0 | 53.8 | 54.5 | 56.5 | 62.1 |
| Rc |  |  | 20 |  |  |

|  | 6 | 7 | 8 | 9 | 10 |
|---|---|---|---|---|---|
| Bar Diameter (in.) | 0.25 | 0.25 | 0.25 | 0.25 | 0.25 |
| e (%) | 89 | 89 | 89 | 89 | 89 |
| Aging Time (h) | 0 | 1 | 1 | 1 | 1 |
| Aging Temp. (°C.) | — | 350 | 400 | 450 | 500 |
| UTS (MPa) | 1142 ± 13 | 1161 | 1151 | 1101 | 1018 |
| YS (MPa) | 1117 ± 21 | 1091 | 1125 | 1083 | 978 |
| Δl (%) | 8 ± 0 | 4 | 3 | 5 |  |
| RA (%) | 20 ± 5 |  |  |  |  |
| E (GPa) | 60.3 ± 17.4 | 56.5 | 53.8 | 61.4 | 66.2 | e = Engineering Strain (% Cold Work)
UTS = Ultimate Tensile Strain
YS = Yield Strength
Δl = Elongation
RA = Reduction in Area
E = Elastic modulus
Rc = Rockwell C hardness As seen from the Table, strength levels up to 1142 MPa were achieved in the "as cold worked" condition. The yield strength increased up to 1117 MPa. Subsequent aging did not further increase the strength of the material, in fact aging at higher temperatures (500° C.) caused a reduction in strength.

EXAMPLE 4

Some 0.75" diameter bars, which had been solution treated and water quenched, were cold swaged to 0.375" and 0.25" diameter, which corresponds to engineering strains of 75% and 89%. The tensile properties of these bars, both with and

TABLE 4

|  | 1 | 2 |
|---|---|---|
| Bar Diameter (in.) | 0.375 | 0.25 |
| e (%) | 75 | 89 |
| Aging Time (h) | 0 | 0 |
| Aging Temp. (°C.) | — | — |
| UTS (MPa) | 1027 ± 6 | 1117 ± 0 |
| YS (MPa) | 938 ± 0 | 1069 ± 0 |
| Δl (%) | 15 ± 1 | 9 ± 1 |
| RA (%) | 49 ± 4 | 23 ± 3 |
| E (GPa) | 52.7 ± 1.4 | 46.0 ± 2.3 | e = Engineering Strain (% Cold Work)
UTS = Ultimate Tensile Strength
YS = Yield Strength
Δl = Elongation
RA = Reduction in Area
E = Elastic modulus Thus, high strengths were achieved in the cold worked condition regardless of whether the starting material was in the hot worked and water quenched condition, or the solution treated and water quenched condition.

EXAMPLE 5

0.007" diameter Ti-13Nb-13Zr wire was produced by annealing in Argon at 1472° F., water quenching, and cold working to produce an engineering strain of 62%. The tensile properties of the wire were as follows:

Ultimate Tensile Strength (UTS)=191 ksi

Yield Strength (YS)=185 ksi

Elastic modulus (E)=7.09 Msi

Thus the Yield Strength/Modulus ratio was 2.61, significantly greater than that of Ti-6Al-4V.

What is claimed is:

1. A low modulus, corrosion resistant dental implant, said implant comprising:

an implant body shaped for implantation beneath gingival tissue of a mouth, cooperation with a jaw bone, and stable fixation relative to said jaw bone, the implant body made of a predominantly alpha-prime hexagonal close packed titanium alloy comprising:
titanium;
from about 10 to about 20 wt. % as the sum of metals selected from the group consisting of niobium and tantalum; and
up to 50 wt. % zirconium,
wherein the alloy is free from deliberately added toxic elements.

2. The dental implant of claim 1, wherein the implant body is an endosteal implant for insertion into a cavity in the jaw bone.

3. The dental implant of claim 1, wherein the implant body is a subperiosteal implant cooperating with outer surfaces of the jaw bone.

4. The implant of claim 1 further comprising a crown, shaped as a tooth-substitute for fixed attachment relative to the implant body, for projecting above a gumline, said crown comprising:
titanium;
from about 10 to about 20 wt. % as the sum of metals selected from the group consisting of niobium and tantalum; and
up to 50 wt. % zirconium.

5. The implant of claim 4, wherein the crown is at least in part made of an alloy that comprises: titanium, from about 10 to about 20 wt. % niobium, and less than about 20 wt. % zirconium.

6. The implant of claim 1 further comprising an abutment at least partially implanted in the jaw bone, the abutment fabricated from an alloy comprising:
titanium;
from about 10 to about 20 wt. % as the sum of metals selected from the group consisting of niobium and tantalum; and
up to 50 wt. % zirconium.

7. The implant of claim 1 further comprising a bridge construct adapted for protruding above a gumline, said construct comprising an alloy comprising:
titanium;
from about 10 to about 20 wt. % as the sum of metals selected from the group consisting of niobium and tantalum;
and up to 50 wt. % zirconium.

8. The implant of claim 1 further comprising an abutment screw for attaching an abutment or dental bridge to the implant body, the screw comprising:
titanium;
from about 10 to about 20 wt. % as the sum of metals selected from the group consisting of niobium and tantalum;
and up to 50 wt. % zirconium.

9. The implant of claim 1 further comprising a macro-textured surface coating at least partially covering outer surfaces of said implant body, said macro-textured surface coating adapted for improving attachment of bony tissue with the outer surfaces.

10. The implant of claim 1 further comprising a coating over at least exposed surfaces of the implant projecting above a gumline to simulate appearance of natural tooth or gold.

11. The implant of claim 1 wherein the alloy is cold worked from about 30 to about 90%.

12. The implant of claim 1 wherein the alloy comprises from about 10 wt. % to about 20 wt. % niobium.

13. The implant of claim 1 further comprising a porous surface coating at least partially covering outer surfaces of said implant body, said porous surface coating adapted for improving attachment of bony tissue with the outer surfaces.

14. A dental device adapted for exposure to corrosive fluids in a mouth of a human, said dental device made from a predominantly alpha-prime hexagonal close packed titanium alloy comprising:
titanium;
from about 10 to about 20 wt. % as the sum of metals selected from the group consisting of tantalum and niobium; and
up to 50 wt. % zirconium;
the dental device remaining in the mouth for a predetermined period of time without release of toxic ions into the mouth, the device having a low modulus of elasticity and
wherein the alloy is free from deliberately added toxic elements.

15. The device of claim 14, wherein the device is a dental bracket for attaching to a tooth and for engagement with an orthodontic wire, and wherein said alloy comprises: titanium, from about 10 to about 20 wt. % niobium, and less than about 20 wt. % zirconium.

16. The device of claim 14 wherein the device comprises an orthodontic wire for attachment to dental brackets, the dental wire having a spring-back ratio of greater than about 2.0.

17. The device of claim 14 wherein the device comprises a buccal tube for use in orthodontics in conjunction with an orthodontic wire, the buccal tube comprising a portion for engaging an orthodontic wire when the buccal tube is attached to a tooth so that the wire exerts a force upon teeth.

18. A low modulus, corrosion resistant dental implant, said implant comprising:

an implant body shaped for implantation beneath gingival tissue of a mouth, cooperation with a jaw bone, and stable fixation relative to said jaw bone, the implant body made of a predominantly alpha-prime hexagonal close packed titanium alloy comprising:
titanium;
from about 35 to about 50 wt. % as the sum of metals selected from the group consisting of niobium and tantalum; and
up to 50 wt % zirconium.
wherein the alloy is free from deliberately added toxic elements.

19. The dental implant of claim 18, wherein the implant body is an endosteal implant for insertion into a cavity in the jaw bone.

20. The dental implant of claim 18, wherein the implant body is a subperiosteal implant cooperating with outer surfaces of the jaw bone.

21. The implant of claim 18 further comprising a crown, shaped as a tooth-substitute for fixed attachment relative to the implant body and for projecting above a gumline, said crown comprising:

titanium;

from about 35 to about 50 wt. % as the sum of metals selected from the group consisting of niobium and tantalum; and up to 50 wt. % zirconium.

22. The implant of claim 21, wherein the crown is at least in part made of an alloy that comprises: titanium, from about 35 to about 50 wt. % niobium, and less than about 20 wt. % zirconium.

23. The implant of claim 18 further comprising an abutment at least partially implanted in the jaw bone, the abutment fabricated from an alloy comprising:

titanium;

from about 35 to about 50 wt. % as the sum of metals selected from the group consisting of niobium and tantalum; and up to 50 wt. % zirconium.

24. The implant of claim 18 further comprising a bridge construct protruding above a gumline, said construct comprising an alloy comprising:

titanium;

from about 35 to about 50 wt. % as the sum of metals selected from the group consisting of niobium and tantalum; and up to 50 wt. % zirconium.

25. The implant of claim 18 further comprising an abutment screw for attaching an abutment or dental bridge to the implant body, the screw comprising:

titanium;

from about 35 to about 50 wt. % as the sum of metals selected from the group consisting of niobium and tantalum; and up to 50 wt. % zirconium.

26. The implant of claim 18 further comprising a macro-textured surface coating at least partially covering outer surfaces of said implant body, said macro-textured surface coating adapted for improving attachment of bony tissue with the outer surfaces.

27. The implant of claim 18 further comprising a coating over at least exposed surfaces of the implant projecting above a gumline to simulate appearance of natural tooth or gold.

28. The implant of claim 18 wherein the alloy is cold worked from about 30 to about 90%.

29. The implant of claim 18 wherein the alloy comprises from about 35 wt. % to about 50 wt. % niobium.

30. The implant of claim 18 further comprising a porous surface coating at least partially covering outer surfaces of said implant body, said porous surface coating adapted for improving attachment of bony tissue with the outer surfaces.

31. A dental device adapted for exposure to corrosive fluids in a mouth of a human, said device made from a predominantly alpha-prime hexagonal close packed titanium alloy comprising:

titanium;

from about 35 to about 50 wt. % as the sum of metals selected from the group consisting of tantalum and niobium; and up to 50 wt. % zirconium;

the dental device remaining in the mouth for a predetermined period of time without release of toxic ions into the mouth, the device having a low modulus of elasticity and wherein the alloy is free from deliberately added toxic elements.

32. The device of claim 31, wherein the device is a dental bracket for attaching to a tooth and for engagement with an orthodontic wire, and wherein said alloy comprises: titanium, from about 35 to about 50 wt. % niobium, and less than about 20 wt. % zirconium.

33. The device of claim 31 wherein the device comprises an orthodontic wire for attachment to dental brackets, the dental wire having a spring-back ratio of greater than about 2.0.

34. The device of claim 31 wherein the device comprises a buccal tube for use in orthodontics in conjunction with an orthodontic wire, the buccal tube comprising a portion for engaging an orthodontic wire when the buccal tube is attached to a tooth so that the wire exerts a force upon teeth.

35. The device of claim 31 wherein the device is an abutment screw for clamping an abutment to a jawbone implant.

36. The device of claim 31 wherein the device is an abutment for affixing to a jawbone implant.

37. The device of claim 14 wherein the device is an abutment screw for clamping an abutment to a jawbone implant.

38. The device of claim 14 wherein the device is an abutment for affixing to a jawbone implant.

39. The dental device of claim 14, wherein the alloy is cold worked from about 30% to about 90%.

40. The dental device of claim 31, wherein the alloy is cold worked from about 30% to about 90%.

* * * * *